United States Patent
Hesketh

(10) Patent No.: US 9,423,068 B2
(45) Date of Patent: Aug. 23, 2016

(54) MOBILE DEVICE AND METHOD FOR SUPPLY OF OZONATED LIQUID

(76) Inventor: Joseph J. Hesketh, Liverpool (GB)

(*) Notice: Subject to any disclaimer, the term of this patent is extended or adjusted under 35 U.S.C. 154(b) by 214 days.

(21) Appl. No.: 14/131,935

(22) PCT Filed: Jun. 27, 2012

(86) PCT No.: PCT/GB2012/051502
§ 371 (c)(1),
(2), (4) Date: Mar. 18, 2014

(87) PCT Pub. No.: WO2013/007979
PCT Pub. Date: Jan. 17, 2013

(65) Prior Publication Data
US 2014/0224336 A1    Aug. 14, 2014

(30) Foreign Application Priority Data
Jul. 14, 2011    (GB) .................................... 1112118.3

(51) Int. Cl.
*C02F 1/78*    (2006.01)
*F16M 13/00*    (2006.01)
*A61L 2/18*    (2006.01)

(52) U.S. Cl.
CPC .............. *F16M 13/005* (2013.01); *A61L 2/183* (2013.01); *C02F 1/78* (2013.01); *A61L 2202/16* (2013.01); *A61L 2202/25* (2013.01); *Y10T 137/0318* (2015.04); *Y10T 137/6855* (2015.04)

(58) Field of Classification Search
CPC ........................................................ C02F 1/78
USPC .................. 261/36.1, DIG. 42; 210/192, 760; 62/264
See application file for complete search history.

(56) References Cited

U.S. PATENT DOCUMENTS

| | | | |
|---|---|---|---|
| 4,619,763 A | 10/1986 | O'Brien | |
| 5,824,243 A | 10/1998 | Contreras | |
| 5,853,014 A | 12/1998 | Rosenauer | |
| 6,186,170 B1* | 2/2001 | Koganezawa | C01B 13/10 137/563 |
| 6,279,589 B1 | 8/2001 | Goodley | |
| 6,585,898 B1 | 7/2003 | Ekberg et al. | |
| 6,964,739 B2 | 11/2005 | Boyd et al. | |
| 2005/0163678 A1 | 7/2005 | Clawson et al. | |
| 2005/0236338 A1 | 10/2005 | Minnix | |
| 2011/0283730 A1* | 11/2011 | Tudor | F24F 3/1405 62/264 |

FOREIGN PATENT DOCUMENTS

| | | |
|---|---|---|
| CA | 2463197 | 10/2004 |
| JP | H07241332 | 9/1995 |
| JP | H1121960 | 1/1999 |
| JP | 2001187120 | 7/2001 |
| JP | 2005186067 | 7/2005 |

OTHER PUBLICATIONS

International Search Report and Written Opinion PCT/GB2012/051502, dated Nov. 19, 2012, 8 pages.

* cited by examiner

*Primary Examiner* — Robert A Hopkins
(74) *Attorney, Agent, or Firm* — Dority & Manning, P.A.

(57) ABSTRACT

A device and method for supplying ozonated liquid is disclosed. Liquid in a reservoir is pumped from the reservoir to a separate ozone generator and is thereby ozonated. The ozonated liquid is retained to the reservoir so that the liquid is circulated in a loop. As the liquid is circulated through the ozone generator, the concentration of ozone increases. Once the liquid has been sufficiently ozonated, the generator is disconnected and the reservoir moved to where ozonated water is required and ozonated water is dispensed from the reservoir.

21 Claims, 7 Drawing Sheets

MOBILE DEVICE AND METHOD FOR SUPPLY OF OZONATED LIQUID

CROSS REFERENCE TO RELATED APPLICATIONS

This application is the U.S. National Stage entry of International Application No. PCT/GB2012/051502 filed under the Patent Cooperation Treaty having a filing date of Jun. 27, 2012, which claims priority to GB Patent Application No. 1112118.3 having a filing date of Jul. 14, 2011.

The present invention is concerned with provision of ozonated liquid. Ozone, both in its gaseous state and in aqueous solution, is a powerful biocide. it is currently used to disinfect equipment in wineries and breweries, in disinfecting water in swimming pools and spas, and in washing fruit and vegetables.

The present inventors consider that ozonated water could safely be used in a range of other sanitizing applications if it could be provided sufficiently economically and conveniently and in a sufficiently high concentration. In hospitals and other institutions, for example, there is a pressing need for powerful biocides for use against infectious agents in general and so-called "superbugs"—antibiotic resistant bacteria—in particular. Certain pathogens are known which have resistance to conventional antiseptics, bleaches etc, so that countering them requires some other form of biocide. Ozonated water could be used in tackling these problems.

There are some obstacles to the wider use of ozone as a biocide. It is unstable, decaying to ordinary diatomic oxygen with a half life of approximately 30 minutes in atmospheric conditions. Hence ozone must be generated shortly before it is to be used. There are commercially available, and in some cases portable, ozone generators intended for use in sanitising. An example is the Destroyer Mobile Sanitation Series supplied by McClain Ozone, Inc of Napa, Calif., which provides ozone gas or ozonated water upon demand. The machine is configured to received pressurised water from an external source and also to receive oxygen gas which is converted to ozone using the corona discharge method (which is well known and will not be described herein) and dissolved in the water as it passes through the machine.

Other known methods of generating ozone include the use of ultra violet light.

Such machines are currently too costly to justify their use in generating ozonated water for use in general cleaning/sanitising in institutions such as hospitals and they also suffer from limitations with regard to the concentration of ozone that can be achieved at the point of dispensing, i.e. at the tip of the hose or nozzle.

WO 98/39108 A1 (Med-O-Tech, discloses a cleaning apparatus intended for cleaning a dialysis machine by circulating ozonated water through the machine. The cleaning apparatus is mounted on wheels and has an onboard tank for holding water as well as an ozone generator.

U.S. Pat. No. 6,279,589 (Goodley) discloses an apparatus for cleaning and disinfecting containers such as truck trailers or aeroplane holds. One suggested form of disinfectant is ozonated water, but again it is envisaged that the ozone generator will be carried on the movable apparatus.

These and other prior art devices are potentially expensive because of the need to provide each mobile apparatus used to supply ozonated water with its own ozone generator.

According to a first aspect of the present invention there is a mobile device for supply of ozonated liquid, the device comprising a liquid reservoir, a supply passage which communicates with the reservoir and is connectable to an input of an ozone generator not carried by the device, a return passage which communicates with the reservoir and is connectable to an outlet of an ozone generator and a pump for circulating liquid in a loop in which the liquid passes from the reservoir to the ozone generator through the supply passage and then from the ozone generator back to the reservoir through the return passage, the device further comprising at least one dispensing passage which communicates with the reservoir and is able to be selectively opened to supply ozonated liquid for use.

The mobile device is connectable to the ozone generator, but the generator is not carried by the mobile device. Thus in accordance with the invention, a single ozone generator can service multiple mobile devices.

Preferably, the device comprises an ozone gas destruction system. The ozone gas destruction system may comprise a heated catalyst.

Preferably, the device comprises a refrigeration system to cool the liquid. The liquid may be cooled to a set temperature.

According to a second aspect of the present invention there is a method of supplying ozonated liquid, comprising: providing an ozone generator at a charge station; providing at least one mobile supply device having a reservoir for storing Ozonated liquid and at least one dispensing passage which communicates with the reservoir and is able to be selectively opened to supply ozonated liquid for use; moving the supply device to the charge station; connecting the reservoir to the charge station and charging the reservoir with ozonated liquid; disconnecting the reservoir from the charge station; moving the mobile supply device to a point of use; and dispensing the ozonated liquid for use.

According to a third aspect of the present invention there is a method of supplying ozonated liquid, comprising filling or part-filling a reservoir with liquid; connecting the reservoir to an ozone generator through supply and return passages; pumping the liquid from the reservoir through the supply passage to the ozone generator, so that the liquid passes through the ozone generator and is thereby ozonated, and from the ozone generator back to the reservoir, so that the liquid circulates in a loop; and dispensing ozonated liquid from the reservoir through a dispensing passage.

A specific embodiment of the present invention. will now be described, by way of example only, with reference to the accompanying drawings in which:

FIG. 5 is a side view of the unit along the direction of arrow B in FIG. 1;

Figure 4:
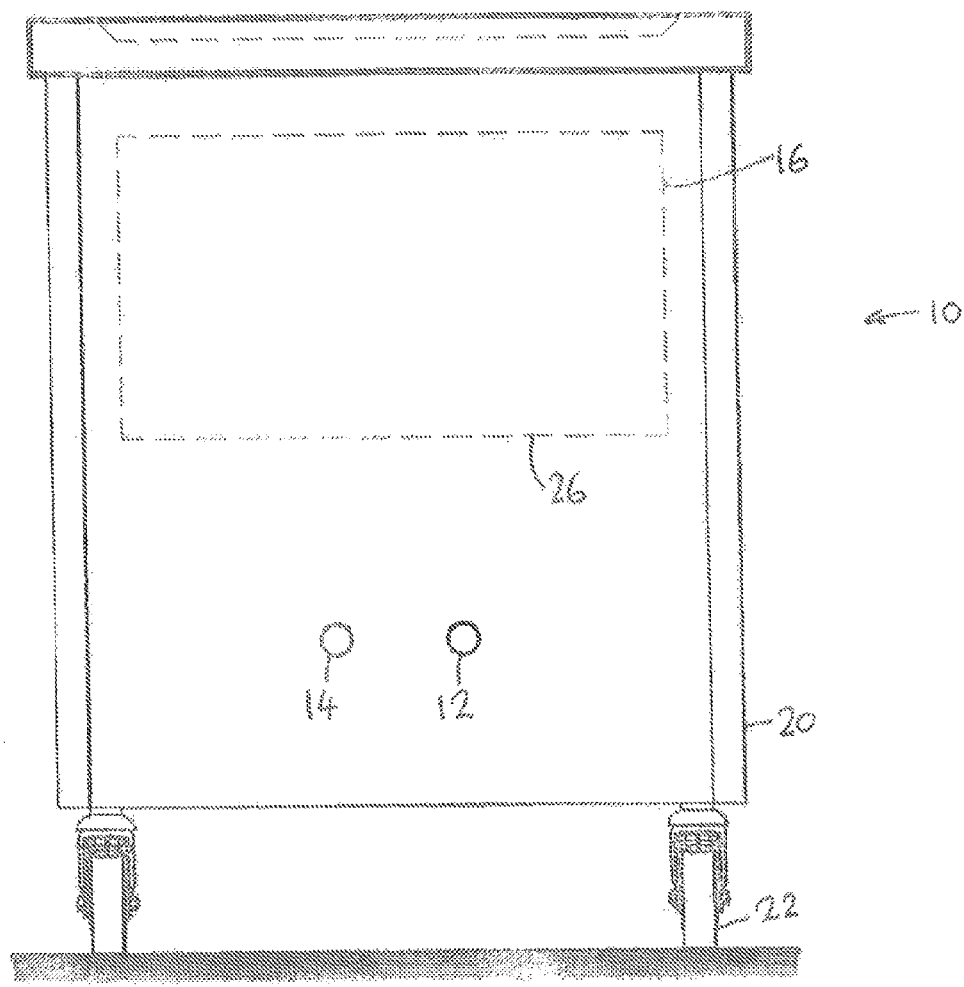
FIG. 4 is an end view of the unit along the direction of arrow A in FIG. 1.

The unit 10 shown in the drawings is used in the generation, storage and supply of ozonated water. It does not include an ozone generator but has generator supply and return pipes 12, 14 (see FIG. 4 in particular) through which a reservoir 16 can be connected to an external ozone generator, which is not shown in the drawings but may for example be the Destroyer from McClain Ozone, Inc., referred to above. Liquid 18 (typically water) is circulated through the ozone generator and so charged with ozone. In accordance with the present invention, the liquid is circulated through the ozone generator repeatedly in a loop, allowing a high ozone concentration to be achieved. Once the liquid 18 in the reservoir has been charged with ozone, the unit 10 can be disconnected from the ozone generator and taken to a point of use (e.g. a hospital ward). The ozone generator can then be used to prepare another, similar, unit for use. In this way one ozone generator can service multiple units 10. Efficient use can thus be made of the relatively expensive ozone generator, reducing costs.

These aspects will now be considered in greater detail, beginning with an explanation of the construction of the unit 10. It is preferred that the unit should be easily moveable by a user and in the illustrated example the unit comprises a wheeled cart whose frame 20 is supported on wheels 22, which are mounted as castors in the illustrated embodiment. A handle 17 at an end of the cart allows it to be easily wheeled by a single user.

The reservoir 16 is supported by the cart frame 20 and elevated by it so that sanitising liquid can be dispensed by gravity feed. The unit provides two means of dispensing the liquid for use.

A dispensing tap 23, opened and closed by means of a lever 24 in the illustrated embodiment, communicates with the reservoir's interior through an opening in bottom wall 26 of the reservoir. Beneath the dispensing tap 23 the frame 20 provides a platform 28 for supporting a receptacle such as a bucket (not shown) while it is filled.

A hose 30 also communicates with the reservoir's interior through an opening in the bottom wall 26 and has a valve handle 32 for actuating a valve (not seen) to control dispensing of liquid. A reel 34 mounted in a space beneath the reservoir 16 stores the hose when not in use. The hose 30 allows the user to deliver ozonated water directly to a point of use.

Figure 1:
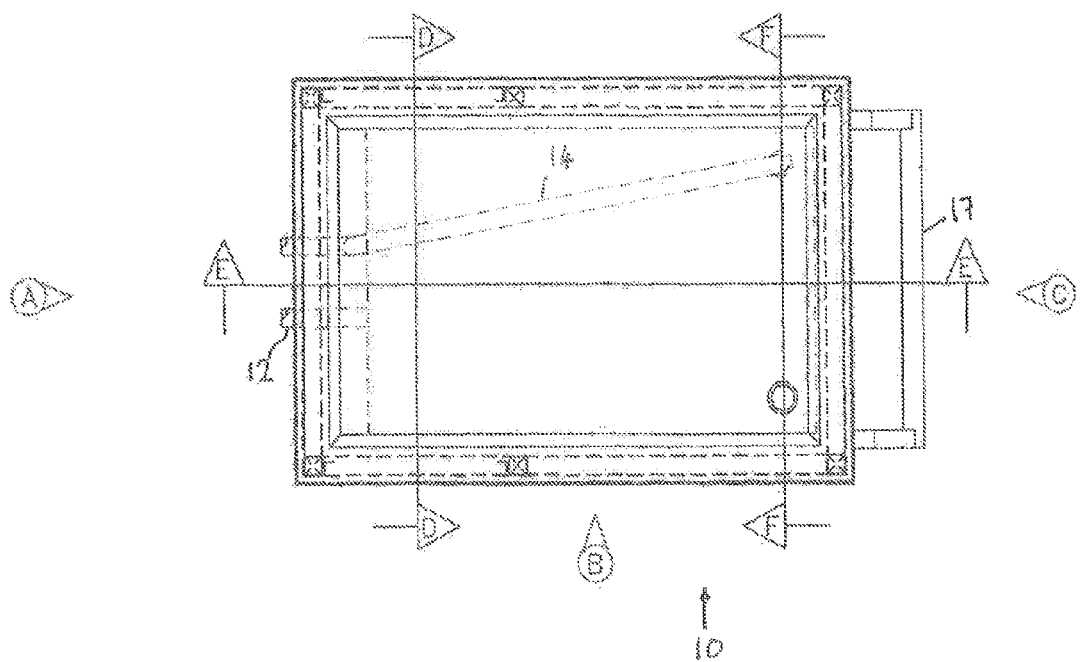
FIG. 1 is a plan view of a unit embodying the present invention.
Figure 2:
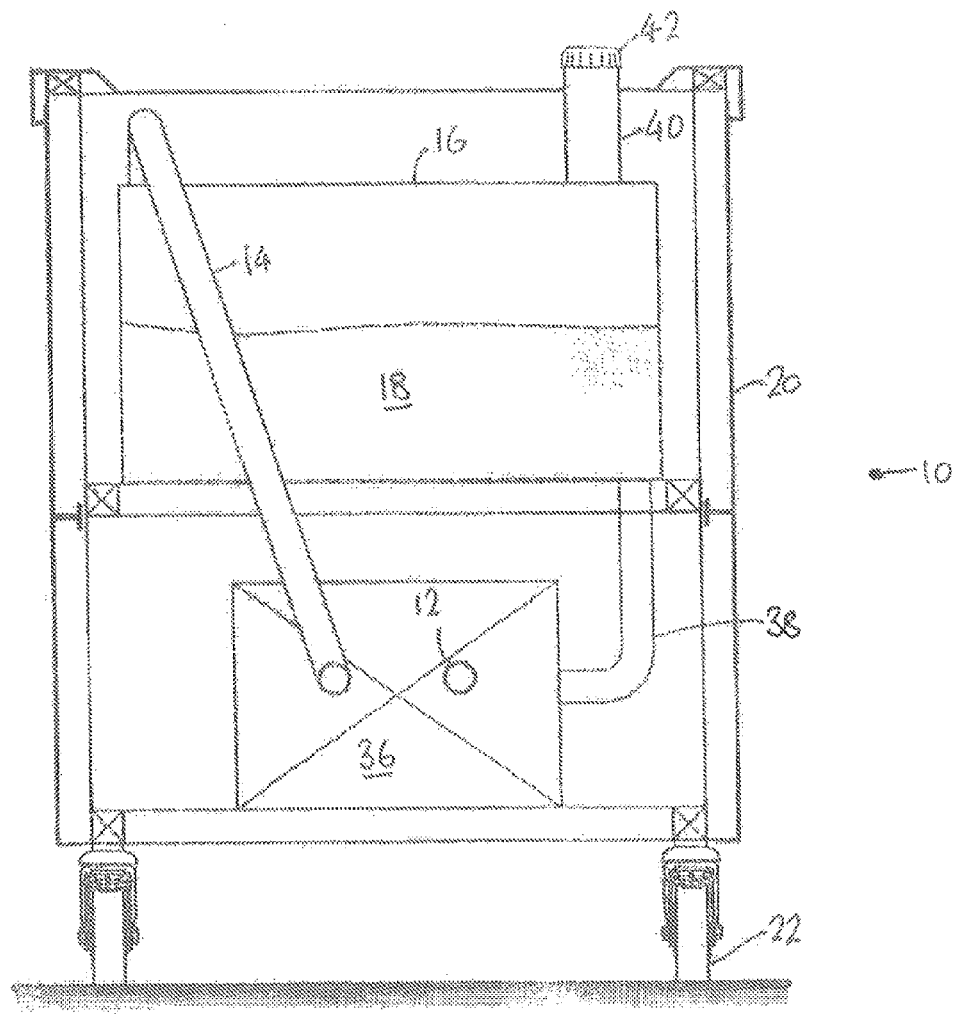
FIG. 2 shows a section through the unit in the plane marked DD in FIG. 1.
Figure 3:
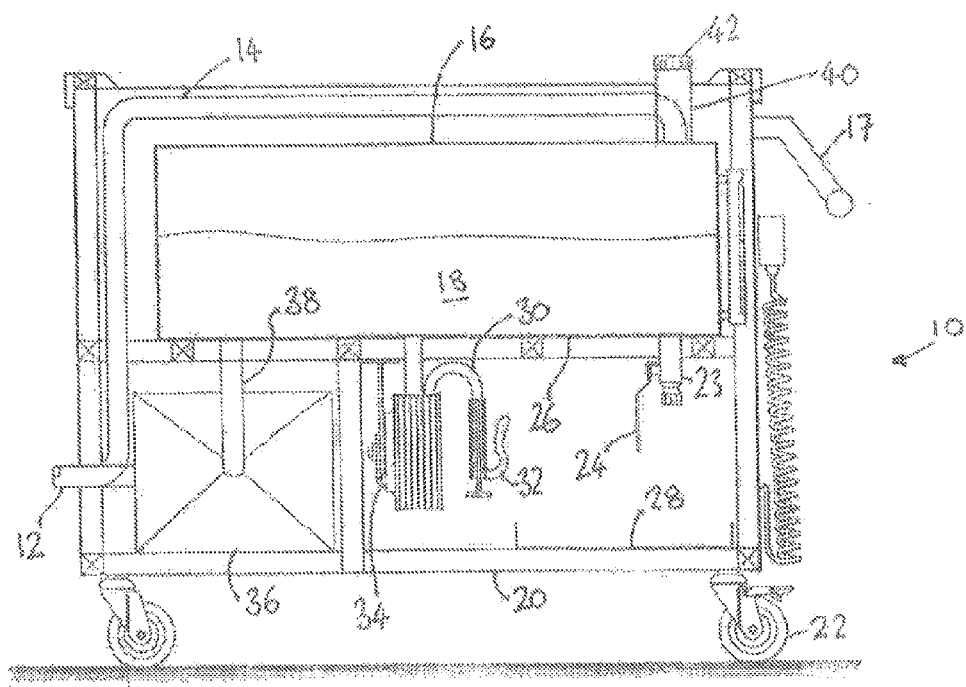
FIG. 3 shows a section through the unit in the plane marked EE in FIG. 1.

The unit 10 comprises a pump 36 which serves to circulate the water while it is being charged with ozone pump supply pipe 38 communicates with the interior of the reservoir through an opening in its bottom wall 26 and leads to the pump 36. The pump's action propels the water out through the generator supply pipe 12 and the water is thus passed to the generator and so ozonated, From the ozone generator, the water passes through the generator return pipe 14 which leads back to the reservoir, as best seen in FIG. 3. By circulating the water in this closed loop for a period of time, the ozone concentration of water in the reservoir 16 is progressively increased and relatively high concentrations can be achieved.

The reservoir 16 needs to be filled with water before use and has an upwardly projecting fill pipe 40 for this purpose. To prevent a vacuum being created as the reservoir is emptied, it is provided with a vacuum relief valve, which is a one way valve which permits air to enter the reservoir 16 when open. The vacuum relief valve is not depicted in the drawings but is incorporated, in the illustrated embodiment, in a removable filler cap 42 used to close the fill pipe 40. A reservoir depth gauge is provided to give the user an indication of the volume of liquid in the reservoir 16. This could take a variety of forms but in the illustrated embodiment it comprises an upright, transparent gauge tube 42 whose ends communicate with the reservoir interior (see FIG. 6). The water level in the gauge tube 42 is visible to the user and the gauge tube may be given markings indicating reservoir liquid volume.

A further one way valve 33, oriented to permit exhaustion of off gas from the reservoir 16, may also be provided to prevent the reservoir 16 from pressurising. Since this valve may serve to vent air with a high ozone concentration the off gas exhausted through it is connected to a heated catalyst which destroys the gas. This may be achieved by connecting the valve's outlet to the generator's off gas destruct system.

There are two phases in the unit's use.

Note first of all that the unit 10 is intended to be mobile. It may for example be used to disinfect items in a hospital. A user would first take the unit 10 to a charge station having an ozone generator. If need be the reservoir 16 would be filled with water. The ozone generator (not shown) would then be connected to the unit 10 and activated, and the pump 36 run to circulate the water through the generator as described above, thereby ozonating the water.

Figure 6:
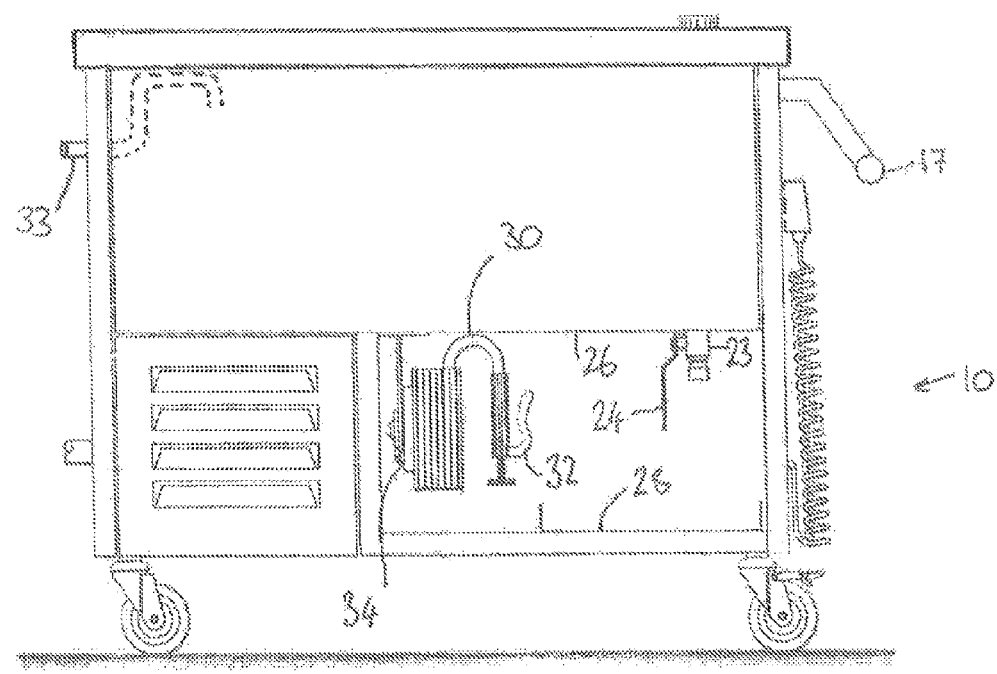
FIG. 6 is a further end view of the unit along the direction of arrow C in FIG. 1.
Figure 6:
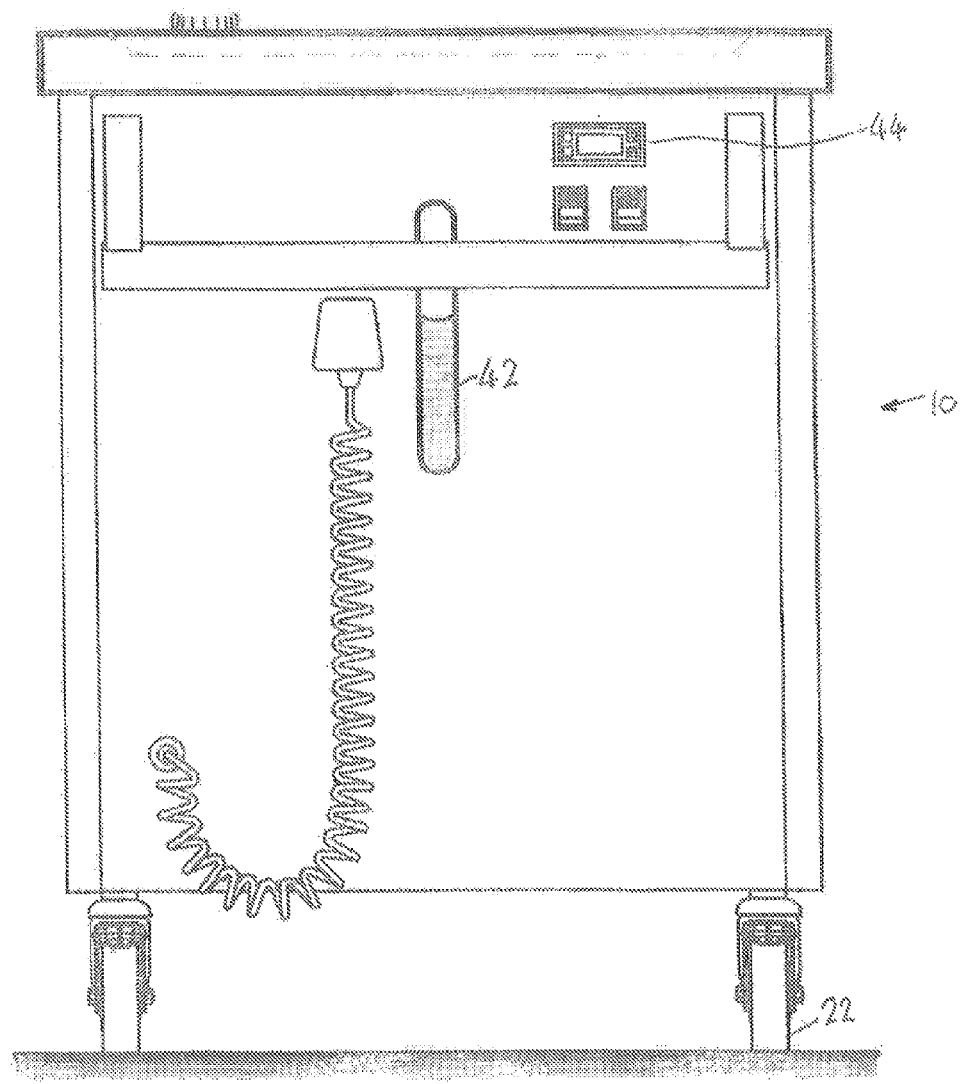
Figure 7:
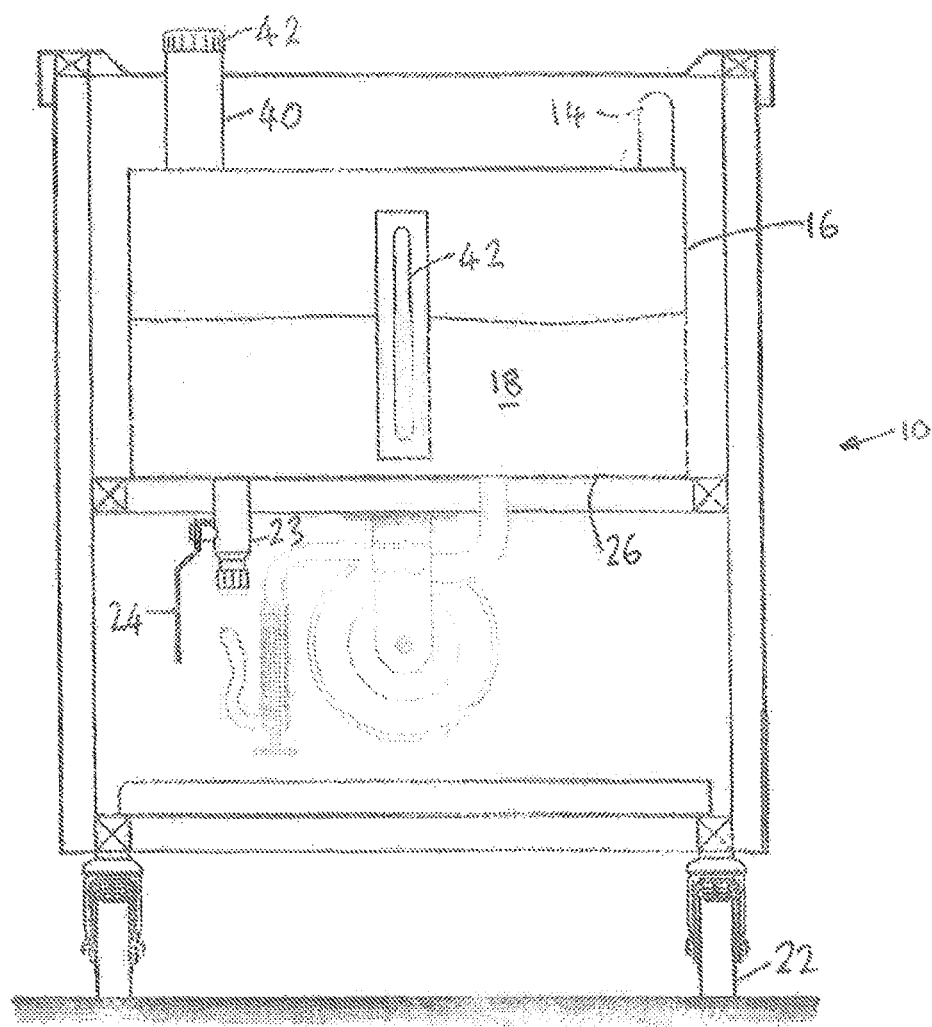
FIG. 7 shows a section through the unit in the plane marked FF in FIG. 1.

Some means of control is required to ensure that an adequate ozone concentration is achieved. This may simply take the form of a timer which causes the pump 36 and the ozone generator to run for a chosen period. FIG. 6 shows a user interface 44 for setting the pump activation period. A more sophisticated approach is to actively monitor ozone concentration, which may be achieved through a sensor (not shown) mounted e.g. in the reservoir 16. In this case the user interface 44 may be used to set a desired ozone concentration so that an associated controller will run the pump 36 and the ozone generator until the desired concentration is achieved. The user interface 44 may be adapted to display the measured ozone concentration, not only to indicate when a required concentration has been achieved but also to enable the user to ascertain, during subsequent use of the ozonated water, whether its ozone concentration has fallen so far as to make it ineffective. An alarm or other signal may for example be triggered when ozone concentration falls below an acceptable level.

In the second phase of the use of unit 10 the ozone generator is disconnected, the unit is wheeled to a point of use (e.g. a hospital ward) and used to dispense Ozonated water for disinfection, general cleaning, sterilisation of equipment or any other suitable purpose. A fleet of units 10 can be serviced by a single ozone generator, greatly reducing the effective cost of provision of the Ozonated water.

Any number of variations to the construction and operation of the unit 10 are possible without departing from the scope of the invention as set out in the appended claims. For instance while the illustrated unit is based upon a wheeled cart, other embodiments could be smaller portable devices, e.g. to be worn in the manner of a rucksack.

Furthermore, the construction of the unit 10 may be arranged so as to accommodate more than one receptacle, such as a mop bucket, or to accommodate one or more receptacles of specific dimensions.

The invention claimed is:

1. A mobile device for supply of ozonated liquid, the device comprising a liquid reservoir, a supply passage which communicates with the reservoir and is connectable to an input of an ozone generator, a return passage which communicates with the reservoir and is connectable to an outlet of an ozone generator not carded by the device and a pump for circulating liquid in a loop in which the liquid passes from the reservoir to the ozone generator through the supply passage and then from the ozone generator back to the reservoir through the return passage, the device further comprising at least one dispensing passage which communicates with the reservoir and is able to be selectively opened to supply ozonated liquid for use, and wherein the reservoir is provided with a gas exhaust passage able to exhaust gas from the reservoir and so prevent it from being pressurized, and wherein the gas exhaust passage is arranged for connection to a gas input of the ozone generator.

2. A mobile device as in claim 1 which is portable or is mounted upon a wheeled frame.

3. A mobile device as in claim 1 further comprising a sensor for sensing ozone concentration in the liquid.

4. A mobile device as in claim 3 further comprising a controller which receives the output of the sensor and is configured to run the device at least until measured ozone concentration reaches a desired value.

5. A mobile device as in claim 1 further comprising a timer configured to run the device for a predetermined time.

6. A mobile device as in claim 1 in which the gas exhaust passage is provided with a one way valve arranged to permit exhaustion of gas from the reservoir and to block entry of gas to the reservoir.

7. A mobile device as in claim 1 further comprising an ozone gas destruction system.

8. A mobile device as in claim 1 further comprising a refrigeration system to cool the liquid.

9. A mobile device as in claim 1 which further comprises a wheeled cart upon which the reservoir is mounted, the reservoir being elevated by the cart enabling liquid to be gravity fed from the reservoir through the dispensing passage.

10. A mobile device as in claim 1 in which the dispensing passage is formed by a flexible hosepipe provided with a user operable valve to control dispensing of the liquid.

11. A mobile device as in claim 9 in which the cart has a platform beneath the reservoir for supporting a receptacle, and the dispensing passage comprises a tap above the platform to dispense liquid into a receptacle on the platform.

12. An apparatus for generating ozonated liquid comprising a device as in claim 1 and an ozone generator connected to the device.

13. A method of supplying ozonated liquid, comprising:
providing an ozone generator at a charge station;
providing at least one mobile supply device as defined in claim 1 having a reservoir for storing ozonated liquid and at least one dispensing passage which communicates with the reservoir and is able to be selectively opened to supply ozonated liquid for use;
moving the supply device to the charge station;
connecting the reservoir to the charge station and charging the reservoir with ozonated liquid;
disconnecting the reservoir from the charge station;
moving the mobile supply device to a point of use; and
dispensing the ozonated liquid for use.

14. A method as in claim 13 in which the mobile supply device comprises a wheeled frame and moving the device comprises wheeling it.

15. A method as in claim 13 in which connecting the reservoir to the charge station comprises connecting a reservoir outlet to an ozone generator inlet and an ozone generator outlet to a reservoir inlet, and circulating liquid through the reservoir and the ozone generator to charge the liquid with ozone.

16. A method as in claim 15 in which the mobile supply device carries a pump for circulating the liquid through the reservoir and the ozone generator.

17. A method as in claim 15 further comprising sensing ozone concentration in the liquid and continuing to circulate the liquid until sensed ozone concentration reaches a predetermined value.

18. A method as in claim 13 further comprising venting excess pressure from the reservoir.

19. A method as in claim 18 further comprising supplying gas vented from the reservoir to an ozone gas destruction system.

20. A method as in claim 13, further comprising cooling liquid in the reservoir.

21. A system for supplying ozonated liquid, comprising at least one mobile device as in claim 1 and an ozone generator connectable to the device to charge its reservoir with ozonated liquid.

* * * * *